(12) United States Patent
Becker et al.

(10) Patent No.: US 7,926,118 B2
(45) Date of Patent: Apr. 19, 2011

(54) VOICE CONTROL WELDING/CUTTING HELMET FUNCTIONS AND SETTINGS

(75) Inventors: William J. Becker, Manitowoc, WI (US); Hans J. Bachmeier, Green Bay, WI (US)

(73) Assignee: Illinois Tool Works Inc., Glenview, IL (US)

( * ) Notice: Subject to any disclaimer, the term of this patent is extended or adjusted under 35 U.S.C. 154(b) by 1147 days.

(21) Appl. No.: 11/646,149

(22) Filed: Dec. 27, 2006

(65) Prior Publication Data

US 2008/0158502 A1 Jul. 3, 2008

(51) Int. Cl.
*A61F 9/06* (2006.01)
(52) U.S. Cl. .......................................................... 2/8.2
(58) Field of Classification Search ................. 2/8, 441, 2/431, 432, 453, 427, 429, 8.2–8.6; 219/147; 349/58; 359/852
See application file for complete search history.

(56) References Cited

U.S. PATENT DOCUMENTS

| | | | |
|---|---|---|---|
| 4,216,367 A | 8/1980 | Risberg | |
| 4,241,286 A | 12/1980 | Gordon | |
| 4,275,266 A | 6/1981 | Lasar | |
| 4,641,292 A | 2/1987 | Tunnell et al. | |
| 5,060,308 A | 10/1991 | Bieback | |
| 5,476,010 A | 12/1995 | Fleming et al. | |
| 5,671,158 A | 9/1997 | Fournier et al. | |
| 6,067,129 A | 5/2000 | Fergason | |
| 6,070,264 A | 6/2000 | Hamilton et al. | |
| 6,242,711 B1 * | 6/2001 | Cooper | 219/130.01 |
| 6,340,234 B1 | 1/2002 | Brown, Jr. | |
| 6,397,186 B1 | 5/2002 | Bush | |
| 6,710,298 B2 * | 3/2004 | Eriksson | 219/130.01 |
| 6,720,878 B2 | 4/2004 | Jumpertz | |
| 6,973,672 B2 * | 12/2005 | Huh | 2/8.1 |
| 6,978,162 B2 | 12/2005 | Russell et al. | |
| 7,053,752 B2 | 5/2006 | Wang et al. | |
| 7,150,047 B2 * | 12/2006 | Fergason | 2/8.1 |
| 7,558,557 B1 * | 7/2009 | Gollnick et al. | 455/343.4 |
| 7,616,771 B2 * | 11/2009 | Lenhardt et al. | 381/326 |
| 7,658,891 B1 * | 2/2010 | Barnes | 422/186.03 |
| 2003/0206491 A1 | 11/2003 | Pacheco | |
| 2005/0002083 A1 | 1/2005 | Fergason | |
| 2005/0007667 A1 | 1/2005 | Fergason | |
| 2005/0017152 A1 | 1/2005 | Fergason | |
| 2005/0097179 A1 | 5/2005 | Orme | |
| 2006/0046845 A1 | 3/2006 | Armand et al. | |
| 2008/0082179 A1 * | 4/2008 | Yang | 700/17 |

FOREIGN PATENT DOCUMENTS

| | | |
|---|---|---|
| EP | 1 010 490 | 12/1999 |
| JP | 05-092788 | 4/1993 |
| JP | 08-254988 | 10/1996 |
| WO | WO 03/026257 A1 | 3/2003 |

* cited by examiner

*Primary Examiner* — Shaun R Hurley
*Assistant Examiner* — Andrew W Sutton
(74) *Attorney, Agent, or Firm* — Fletcher Yoder, PC (57) ABSTRACT

Provided for is a control system for a welding helmet comprising: an electronically controllable lens configured to be mounted in a welding helmet shell, a microphone configured to receive an audible input and to generate a signal in response to the audible input received and an electronic control module coupled to the lens and to the microphone and configured to control the electronically controllable lens based upon the signal. Also provided for is a welding helmet implementing a control system and a method of manufacturing a welding helmet including a control system.

24 Claims, 9 Drawing Sheets

VOICE CONTROL WELDING/CUTTING HELMET FUNCTIONS AND SETTINGS

BACKGROUND

The present invention relates generally to welding helmets and, more particularly, to the control methods by which the user adjusts settings of functions within a welding helmet.

Welding operations are generally performed with certain precautions due to the potential exposure of the welding operator to high heat, flames, weld spatter and ultraviolet light. For example, in arc welding, an arc may provide extremely bright emissions in the weld area that may lead to a condition known as "eye arc" in which ultraviolet light causes the inflammation of the cornea and can burn the retina of the eyes if they are unprotected. To prevent such a condition, goggles and helmets are worn by welders. These helmets generally include a face plate (or lens) that is darkened to prevent or limit exposure to the arc light. In some helmets, the lens is constantly dark with the user flipping down the helmet during welding. In other helmets, the lens may change from a clear state to a darkened state. For example, a user may "turn on" the lens to a constant darkened state, or the lens may automatically darken when it detects bright light that is in excess of a threshold value. Further, such welding helmets may provide for adjustment of the threshold value to trigger the lens change, as well as adjustment of a time delay for transitioning between darkened and clear states. For example, the user may remove the helmet and adjust a dial to provide for a threshold light limit, shade level, or delay from the time the arc is extinguished until the lens returns to a clear state.

In certain welding applications, it may be desirable for the welder to frequently change the state of the lens from a light state to a dark state or vice versa, or to adjust the settings of the helmet. For example, during welding, the welder may frequently need a clear state between welds to inspect the weld, or a welder may need to modify the settings to darken the helmet to avoid exposure to light generated by another nearby welder. In these instances, it may be time consuming and laborsome for the welder to manually adjust the settings of the lens. Accordingly, it may be desirable that a welding helmet include features that allow simpler and more flexible command of helmet settings and functions.

BRIEF DESCRIPTION

In accordance with one aspect of the present invention, a welding helmet includes a helmet shell; an electronically controllable lens mounted to the shell; a microphone configured to receive an audible input and to generate a signal in response to the audible input received. An electronic control module is coupled to the lens and to the microphone and configured to control the electronically controllable lens based upon the signal.

In accordance with another aspect of the present invention, a control system for a welding helmet includes an electronically controllable lens configured to be mounted in a welding helmet shell; a microphone configured to receive an audible input and to generate a signal in response to the audible input received. An electronic control module is again coupled to the lens and to the microphone and configured to control the electronically controllable lens based upon the signal.

A method is also provided for manufacturing a welding helmet. The method includes mounting an electronically controllable lens assembly in a helmet shell; and mounting a microphone in the helmet shell. The microphone is configured to receive an audible input and to generate a signal indicative of the audible input. A control module is mounted to the helmet shell, and is coupled to the electronically controllable lens and configured to control the electronically controllable lens based upon the signal.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
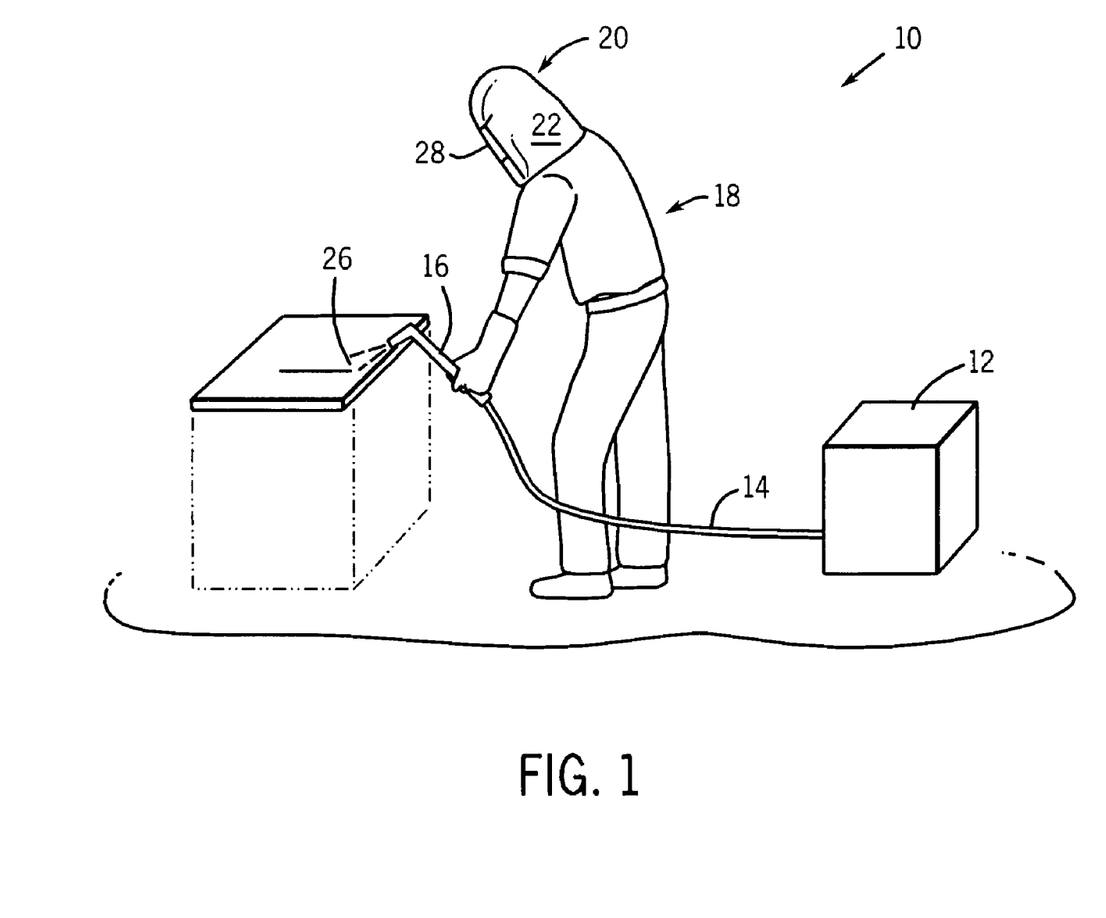
FIG. 1 is an illustration of an exemplary arc welding system including a welding helmet in accordance with aspects of the present technique.

The present invention may have uses in a variety of welding applications. For example, FIG. 1 illustrates an arc welding system 10. As depicted, the arc welding system 10 may include a power supply 12 that generates and supplies a current to an electrode 16 via a conduit 14. In the arc welding system 10, a direct current (DC) or alternating current (AC) may be used along with a consumable or non-consumable electrode 16 to deliver the current to the point of welding. In such a welding system 10, an operator 18 may control the location and operation of the electrode 16 by positioning the electrode 16 and triggering the starting and stopping of the current flow.

In welding operations employing welding system 10 depicted in FIG. 1, welding is generally performed with certain precautions due to the generation of heat, and bright light in visible and non-visible spectra. To avoid overexposure to such light, a helmet assembly 20 is worn by the welding operator 18. The helmet assembly 20 includes a helmet shell 22 and a lens assembly 24 that may be darkened to prevent or limit exposure to the light generated by the welding arc, as discussed below.

When the operator 18 applies current from the power supply 12 to electrode, and begins the welding operation, an arc 26 is developed between the electrode and a work piece. The conduit 14 and the electrode 16 thus deliver current and voltage sufficient to create the electric arc 26 between the electrode 16 and the work piece. The arc 26 melts the metal (the base material and any filler material added) at the point of welding between electrode 16 and the work piece, thereby providing a joint when the metal cools. The welding systems 10 may be configured to form a weld joint by any known technique, including shielded metal arc welding (i.e., stick welding), metal inert gas welding (MIG), tungsten inert gas welding (TIG), gas welding (e.g., oxyacetylene welding), and/or resistance welding.

As described below, helmet assemblies in accordance with the present invention include a lens assembly that may include functionality to transition a lens 28 from a clear state to a darkened state. Generally, a lens assembly that transitions from a clear to darkened state may include a lens including a LCD layer that darkens when a voltage is applied across the layer. For example, a user may "turn on" the lens to provide a voltage across the lens and cause the lens to transition from a light or relatively clear state to a darkened state.

As described below, in particular embodiments, the lens assembly may include a lens 28 and associated electronic components to cause the lens to automatically darken when sensors detect bright light that is in excess of a threshold value, triggering circuitry of the lens assembly to provide a voltage across the lens. In addition to darkening the lens, helmets in accordance with the invention may provide for adjustment of the threshold value of sensed light that triggers the lens to transition between light and dark states. For example, the circuitry of the helmet assembly may include a circuit designed to allow for adjustment of the sensitivity of the helmet sensors and circuitry to light, and thereby set the level of external light that triggers the transition of the lens between states. Further, a time delay for transitioning between the darkened and clear states may be set by the user. Such a setting may govern the time delay between detecting that the arc is extinguished and transition of the state of the lens from its dark state to its clear state.

Figure 2:
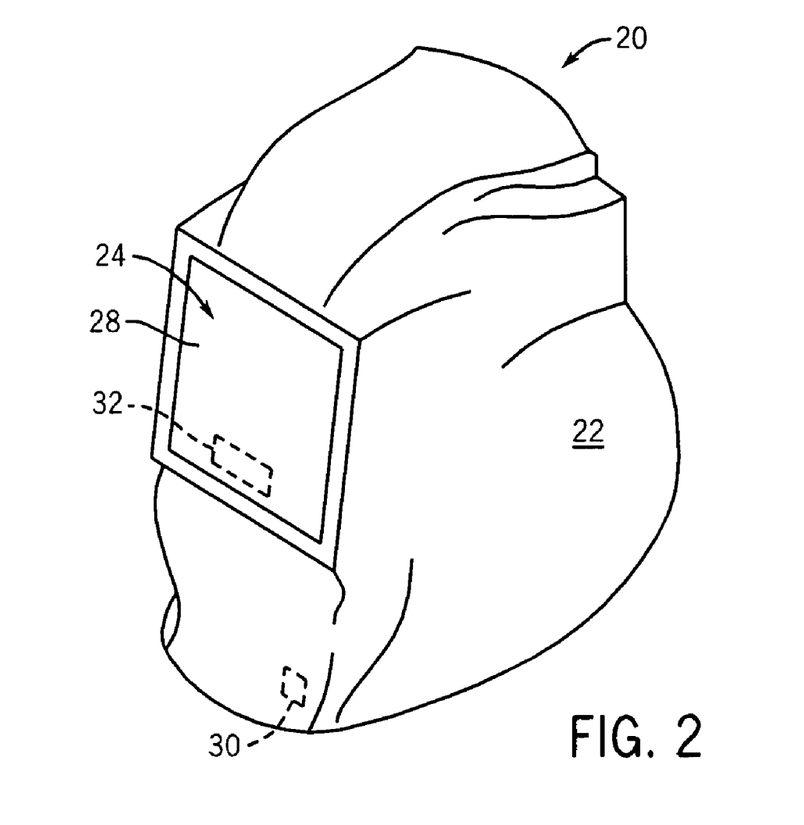
FIG. 2 is an illustration of an exemplary embodiment of the welding helmet of FIG. 1 including a microphone in accordance with aspects of the present technique.

To simplify the use of welding helmet assembly 20, the present invention allows for a voice control feature that may provide for audible selection and adjust of common features of the welding helmet assembly. Embodiments of this invention, including those discussed in detail below, may provide for adjusting settings in real-time while welding, and may also provide for adjusting settings without removing the helmet assembly 20. For example, as depicted in FIG. 2, a welding helmet assembly 20 will include, in addition to a helmet shell 22 and lens assembly 24, a microphone 30, and a lens control module 32. The microphone 30 may be incorporated into the lens control module 32, or may be separate from it.

Certain of the settings of the welding helmet assembly 20 may be pre-set at the time of manufacture, and may be re-adjusted by the operator 18. In particular, functions of the helmet assembly 20 may have adjustable settings controlled by manually adjusting analog or digital knobs, sliders, switches, buttons, and so forth. Accordingly, to make adjustments to the settings, an operator 18 may adjust the settings prior to welding, and/or re-adjust the settings once welding has begun.

As depicted by FIG. 2, the helmet shell 22 may constitute the general frame and support for the components of the welding helmet assembly. For example, the helmet shell 22 provides a partial enclosure about the face of the operator 18 and neck to shield the operator from exposure to the high heat and bright light produced during welding. In addition to providing general protection, the helmet shell 22 provide a location to mount a lens assembly 24 and any additional accessories or control circuitry discussed in more detail below (e.g., lens control module 32 or a secondary control module 40 of FIG. 13).

The lens control module 32 may include circuitry configured to monitor and control the state of the lens 28, as well as circuitry to control other functions of the helmet assembly 20. In one embodiment, the lens control module 32 may be provided as component of the lens assembly 24. For example, the lens assembly 24 may be mounted to the helmet shell 22 as a single unit. In another embodiment, the lens control module 32 may be a component that is separate from the lens assembly 24 and the lens 28. For example, where the lens control module 32 is separate from the lens assembly 24, it may be mounted remotely in the helmet shell 22 with a connection (e.g., via wire conductors) to the lens assembly 24 sufficient to transmit control signals. As will be discussed in further detail, the lens control module 32 may acquire various inputs (e.g., microphone 30 or manual inputs 36), process the inputs, compare the inputs to the values stored in a memory and carry out programmed functionality to provide corresponding outputs to accessories related to the welding helmet assembly 20, particularly to lighten and darken the lens.

As an additional component of the welding helmet assembly, the microphone 30 may be configured to receive voice commands as an input to the lens control module 32. In one embodiment, the microphone 30 may be mounted to the helmet shell 22 in a location convenient to receive voice commands from an operator 18. For example, as depicted in FIG. 2, the microphone 30 may be located near the portion of the helmet shell 20 covering the mouth of the operator 18. The proximity of the microphone 30 to the mouth of the user may provide for audible commands of the operator 18 to be sensed by the microphone 30. As will be appreciated by those skilled in the art, the location of the microphone 30 may vary to meet requirements of specific applications. For example, the microphone 30 may be located remotely in the helmet shell 22, within the lens control module 32, or may be within additional circuitry of the helmet assembly 20.

Figure 3:
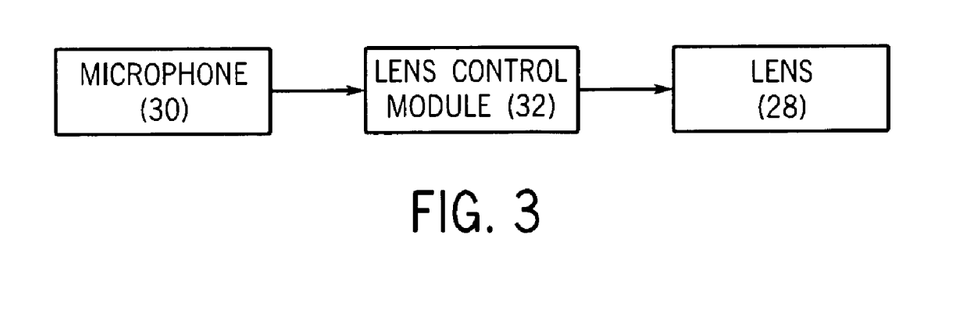
FIG. 3 is a diagrammatical illustration of the exemplary embodiment of the welding helmet of FIG. 2 in accordance with aspects of the present technique.

As depicted in the diagram of FIG. 3, the microphone 30 communicates with the lens control module 32 to facilitate audible control of the lens assembly 24. In one embodiment, the microphone 30 may sense an audible command by the operator 18, and output a signal indicative of the command sensed. For example, the microphone 30 may detect a command and output a raw or amplified analog waveform signal representative of the command detected. The signal may then be transmitted to the lens control module 32 for processing. The lens control module 32 may then process the signals from the microphone 30 and provide an output to the lens 28 based on the result of the processing and functions stored in memory. For example, the lens control module 32 may implement voice recognition processing to interpret a signal from the microphone 30 and determine that the audible command from the operator 18 was "dark." Accordingly, the lens control module 32 may output a signal to the lens 28 which is configured to darken the lens. As an additional example, if the sensitivity of the lens 28 is too low such that the lens has not darkened, an operator 18 may issue an audible command (e.g., "dark") to increase the sensitivity until the lens 28 darkens. The new sensitivity setting may remain as a setting even after the arc 26 is extinguished. As will be appreciated by those skilled in the art, other commands may be sensed and processed based on the functions and settings of the helmet assembly 20. For example, the lens control module 32 may interpret the command "sensitivity" followed by the words "more" or "less" to make adjustment to sensitivity setting of an auto-darkening helmet assembly 20.

Although some embodiments may include voice recognition processing in the lens control module 32, the processing may be completed separate from the lens control module 32. In one embodiment, the microphone 30 may include voice recognition processing to interpret the audible command and output a representative signal. For example, the microphone 30 may be configured to sense a command from a user, provide voice recognition processing and transmit a corresponding digital signal to the lens control module 32 for subsequent processing. As will be appreciated by those skilled in the art, various techniques and software for voice recognition currently exists, and may be implemented in any location and manner that provides for the processed voice command to control functions related to the welding helmet assembly 20.

Figure 4:
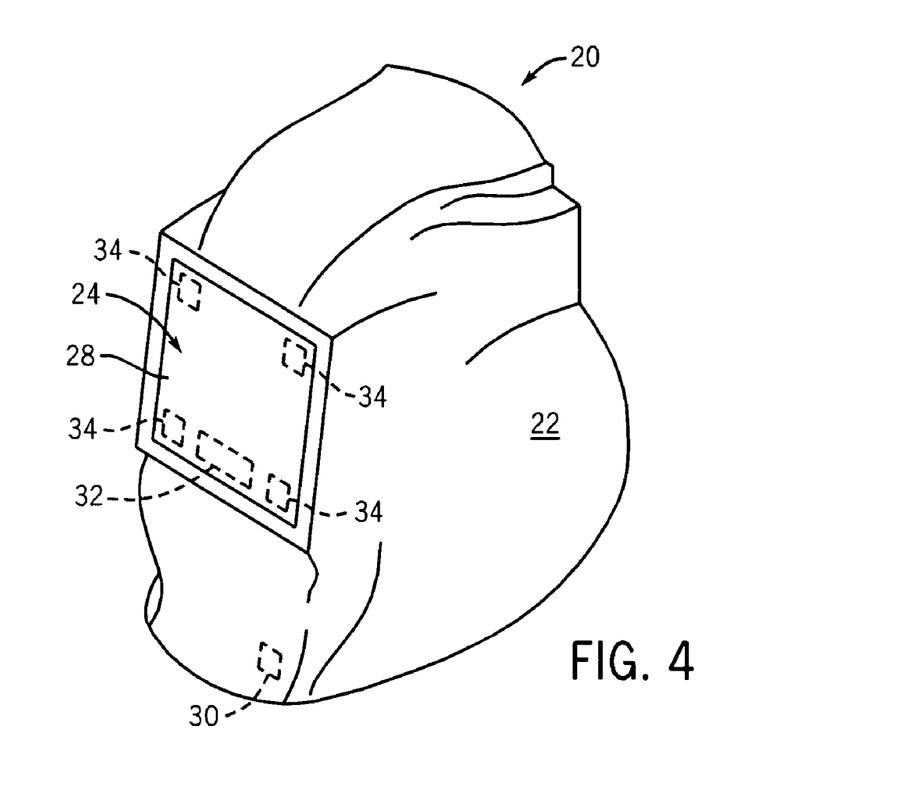
FIG. 4 is an illustration of an alternate exemplary embodiment of the welding helmet of FIG. 1 including arc sensors in accordance with aspects of the present technique.
Figure 5:
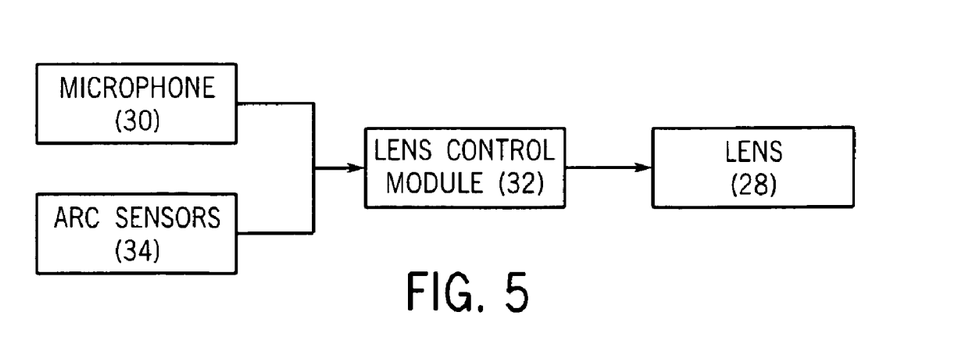
FIG. 5 is a diagrammatical illustration of the exemplary embodiment of the welding helmet of FIG. 4 in accordance with aspects of the present technique.

In addition to using an audible command to implement functions of the helmet assembly 20, an auto-darkening welding helmet assembly 20 may include arc sensing circuitry that is responsive to the level of light created by the arc 26. For example, as depicted in FIG. 4, the lens assembly 24 may include arc sensors 34 about the periphery of the lens 28. In one embodiment, the arc sensors 34 may include photodetectors configured to sense the light of the arc 26. In another embodiment, the arc sensors 34 may include electromagnetic sensors configured to detect the electromagnetic emissions of the arc 26. The arc sensors 34 may determine the intensity of the light experienced at the lens 28, and output a signal indicative of the light intensity to the lens control module 32. Based on the signal provided by the sensors 34, the lens control module 32 may output a signal to the lens 28 to change to a light or dark state. In one embodiment, the signals provided by the microphone 30 and the arc sensors 34 may be simultaneously monitored by the lens control module 32 (see FIG. 5). For example, the lens control module 32 may command a dark lens 28 if either of the microphone 30 or arc sensors 34 provide a signal to that requires the lens to be darkened (e.g., an audible command or light above a threshold value). In another embodiment, the lens control module 32 may be configured to give priority to one input over another. For example, to ensure that the lens 28 is darkened when an arc 26 is present, the lens control module 32 may darken the lens even if the last audible command to the microphone 30 was for a clear lens 28. In another embodiment, to prevent inadvertent clearing of the lens 28 during welding, the lens control module 32 may not respond to command signals to clear the lens 28 while the arc sensors 34 detect an arc.

Although measures such as auto-darkening may be beneficial, there may be times when the operator 18 needs to override the light or dark status of the lens 28 or commands from the control circuitry. In one embodiment, the operator 18 may be able to override the darkened state. For example, during the detection of an arc 26, and darkened state of the lens 28, the user may be able to command "override" and "clear" to return the lens 28 to a clear state. This may be useful when the sensitivity of the lens control module 32 has been set low, and the lens 28 darkens prematurely. As will be appreciated by those skilled in the art, the priority of each function may be manipulated to provide desired functionality of the helmet assembly 20.

Figure 6:
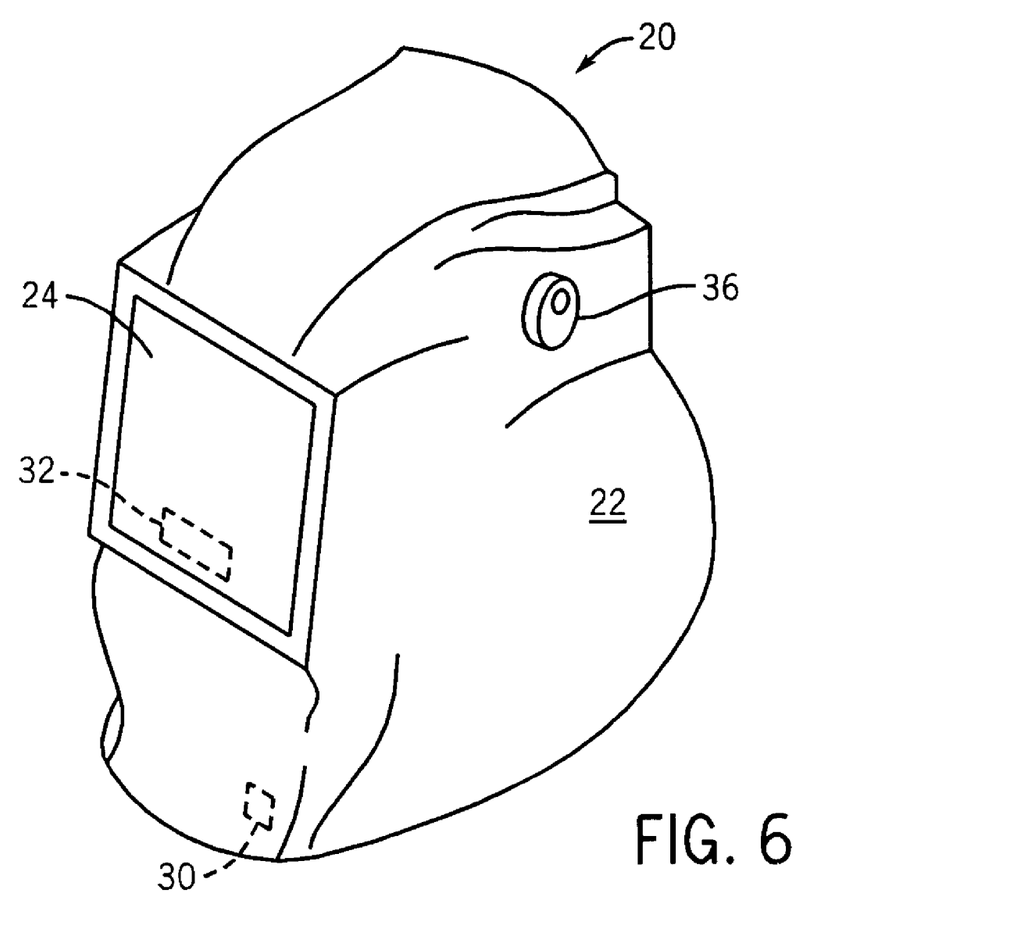
FIG. 6 is an illustration of yet another exemplary embodiment of the welding helmet of FIG. 1 including a manual input in accordance with aspects of the present technique.

In addition to providing hands-free operation of the welding helmet assembly 20, it may also be desirable that the helmet assembly 20 includes a manual input to select and fine tune functions or settings of the welding helmet assembly 20. As depicted in the embodiment of FIG. 6, the manual input 36 may include a dial secured to the exterior of the helmet shell 22 that provides a signal when the dial is manipulated by the operator 18. As will be appreciated by those skilled in the art, the manual input 36 may take any form which provides a corresponding signal in response to the input of the operator 18. For example, the manual input 36 may include a digital encoder, a knob, a touch sensitive sensor and/or one or more buttons or keys.

Figure 7:
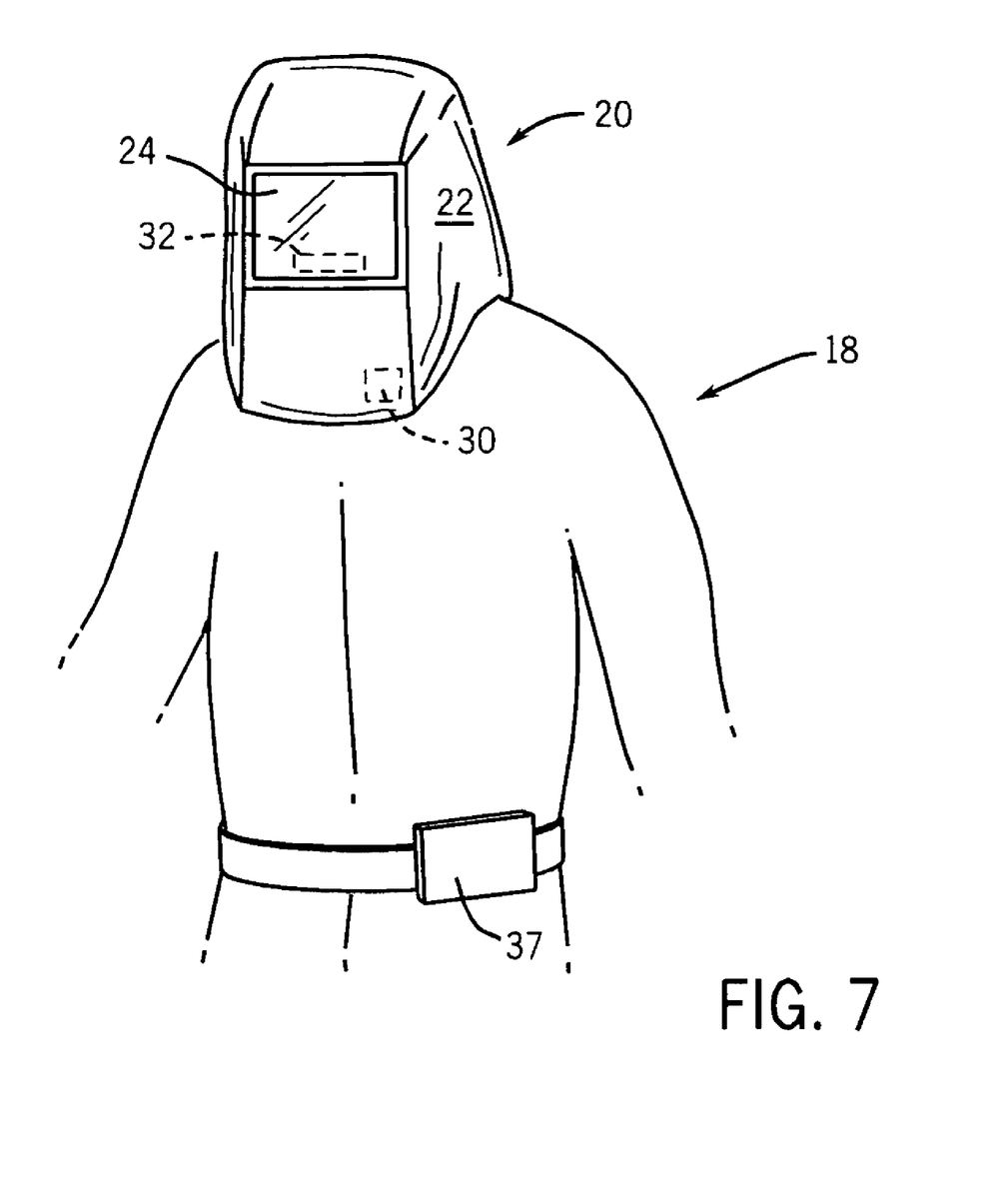
FIG. 7 is an illustration of an exemplary embodiment of the welding helmet of claim 6 including a remote control manual input in accordance with aspects of the present technique.
Figure 8:
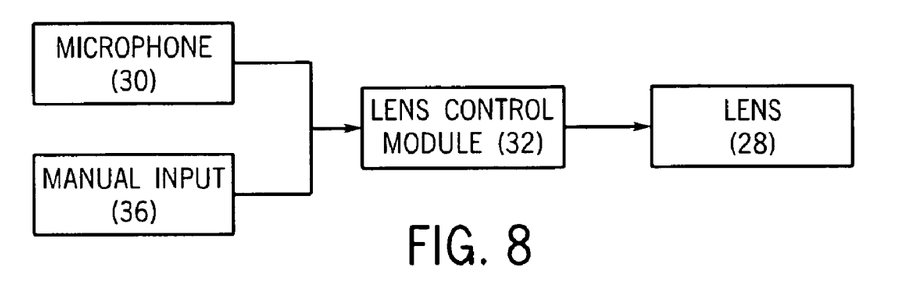
FIG. 8 is a diagrammatical illustration of the exemplary embodiment of the welding helmet of FIGS. 6 and 7 in accordance with aspects of the present technique.

In another embodiment, as depicted in FIG. 7, the manual input 36 may include a wired or wireless remote control 37 worn by the operator 18. For example, the remote control 37 may include buttons to adjust a variety of settings and functions including those previously and subsequently discussed (e.g., shade, sensitivity, speed of an integrated fan—see FIG. 11, and other options). As depicted in the diagram of FIG. 8, the remote control 37 may transmit the inputs to the lens control module 32, wherein the lens control module 32 is configured to receive and process the inputs, and output an appropriate signal to the lens 28, a heads-up display (HUD) 38 (see FIG. 9), or other helmet function 43. In one embodiment, the remote control 37 may also receive and process signals from the lens control module 32. For example, the lens control module 32 may output the status of helmet functions, and the remote control 37 may display the status of helmet functions (e.g., the status and settings of the lens 28). In yet another embodiment, a function of the remote control 37 may be provided independently or in coordination of a display on the HUD 38. For example, a LED on the remote may indicate that the helmet assembly 20 is powered on, while a numerical indication of the current sensitivity setting is displayed via an LCD of the remote control 37 and the HUD 38.

In operation, the manual input 36 may provide for inputs in conjunction with the microphone 30. As depicted in the diagram of FIG. 8, the lens control module 32 may monitor inputs from both the microphone 30 and the manual input 36, and output an appropriate signal to the lens 28. In one embodiment, the operator 18 may speak a command into the microphone 30 to select the functionality of the manual input 36, followed by the user adjusting the manual input 36. For example, the operator may speak "shade" and then adjust the digital encoder knob to select the desired shade. As will be appreciated by those skilled in the art, the design of the manual input 36 may allow for increased flexibility in adjustment of the settings. For example, a high resolution encoder may provide for very fine adjustment of settings.

In a similar embodiment, the microphone 30 and manual input 36 may provide for simultaneous adjustment of functions and settings. For example, the operator 18 may command to adjust a particular function (e.g., shade), and subsequently adjust the setting for that function with audible commands through the microphone 30 or by manual input 36 (i.e., speak a command "dark" or "light", or adjust the manual input until the desired shade is reached). In another embodiment, the manual input 36 may be used to select a particular function to adjust, and subsequently allow commands spoken into the microphone 30 to make the setting adjustments. For example, the operator may set the manual input 36 to a "shade" position and subsequently command "darker" or "lighter" to change the shade setting. As will be appreciated, the functionality of the microphone 30 and the manual input 36 may be varied in any combination to provide the desired functionality.

Figure 9:
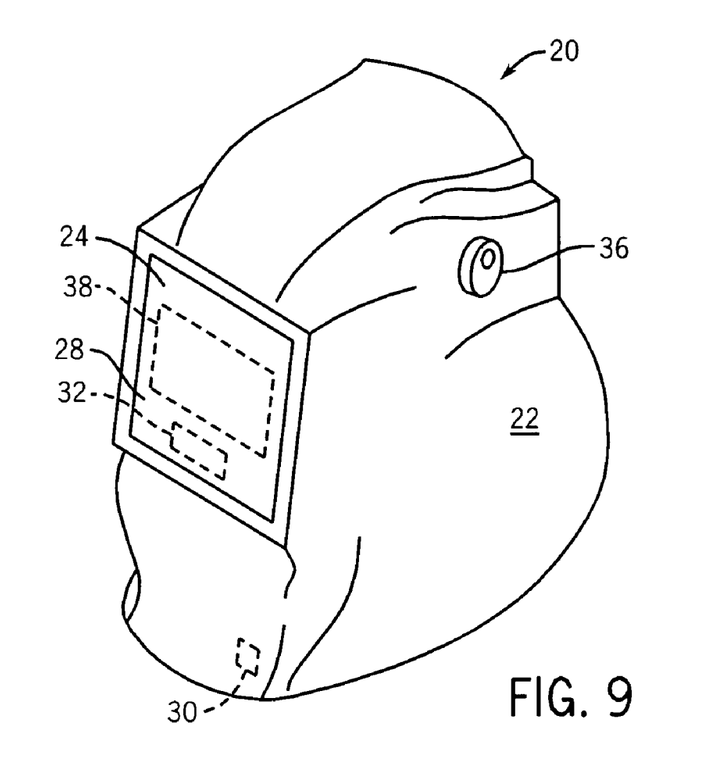
FIG. 9 is an illustration of yet another alternate exemplary embodiment of the welding helmet of FIG. 1 including a heads-up display in accordance with aspects of the present technique.

In addition to providing hands-free adjustments of the welding helmet functions and settings, it may be desirable for information to be readily available to the operator 18. In one embodiment, the welding helmet assembly 20 may include a (HUD) that provides visual information in the line-of-sight (or peripheral vision) of the operator 18. For example, as depicted in FIG. 9, the lens assembly 24 may include a HUD 38 on the lens 28 and in view of the operator 18. In one embodiment, the HUD 38 may include a display of the present settings. For example, the HUD 38 may display the "shade" or "sensitivity" each followed by a corresponding number or symbol (e.g., "50%" or an icon) that indicates the present setting. In another embodiment, the HUD 38 may display the current selections of the operator 18. For example, operator 18 may command "shade" followed by the HUD 38 displaying "shade" to indicate to the operator 18 that the manual input 36 and voice commands are now controlling the "shade" setting. As will be appreciated by those skilled in the art, the HUD 38 may also incorporate displaying information other than functions and settings of the welding helmet assembly 20. For example, the HUD 38 may also display an indication of the status of the welding power supply 12, a clock, the temperature, and so forth. Further, in an environment where a respirator is required, it may also be useful for the HUD 38 to display the surrounding air quality to inform the operator 18 when it may be safe to remove the respirator and welding helmet assembly 20.

Figure 10:
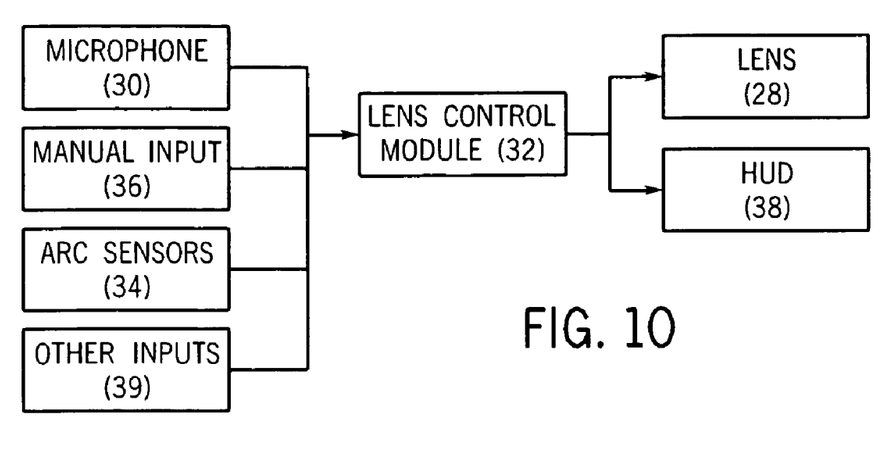
FIG. 10 is a diagrammatical illustration of the exemplary embodiment of the welding helmet of FIG. 9 in accordance with aspects of the present technique.

To provide for the display of information on the HUD 38, the HUD 38 may be controlled by the lens control module 32. In one embodiment, as depicted by the diagram of FIG. 10, the lens control module 32 may monitor inputs from the microphone 30, the manual input 36, the arc sensors 34, and/or other inputs 39 and provide corresponding outputs to the lens 28 and HUD 38. For example, the operator 18 may command "H-U-D shade" which is received by the lens control module 32 via the microphone 30. The lens control module 32 may then process the input from the microphone 30 and send a corresponding signal to the HUD 38 to display the current shade setting. In another embodiment, the HUD 38 may activate when the operator 18 adjusts the manual input 36. For example, the HUD 38 may be configured to display a blank screen until an input is received (e.g., a manual input). In such an embodiment, when the operator 18 turns the knob of the manual input 36, the lens control module 32 may detect the input and provide a signal for the HUD 38 to display the current value of the setting and update the displayed value as the manual input 36 is manipulated. In yet another embodiment, the HUD 38 may be responsive to the arc sensors 34 as depicted in the diagram of FIG. 10. For example, in response to a signal from the arc sensor 34 indicating a light value above the a threshold limit, the lens control module 32 may provide an output to darken the lens 28 and may simultaneously output a signal for the HUD 38 to display an indication that the lens 28 has been auto-darkened (e.g., an icon representative of exceeding the threshold value). As will be appreciated by those skilled in the art, the lens control module 32 may control the lens 28 and HUD 38 based on signals from the microphone 30, manual input 36, arc sensors 34, other inputs 39, or any combination of the like.

Figure 11:
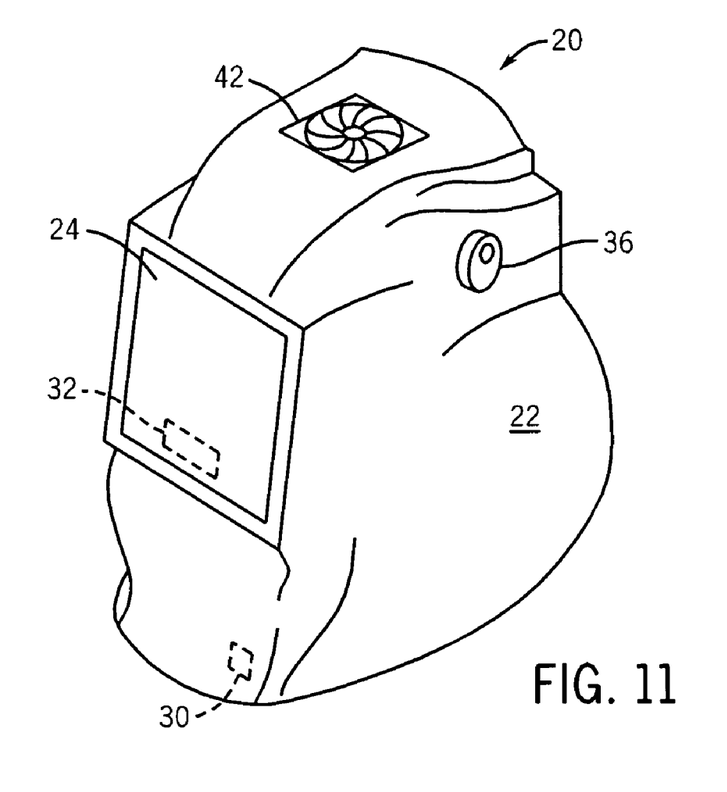
FIG. 11 is an illustration of yet another alternate exemplary embodiment of the welding helmet of FIG. 1 including a fan in accordance with aspects of the present technique.
Figure 12:
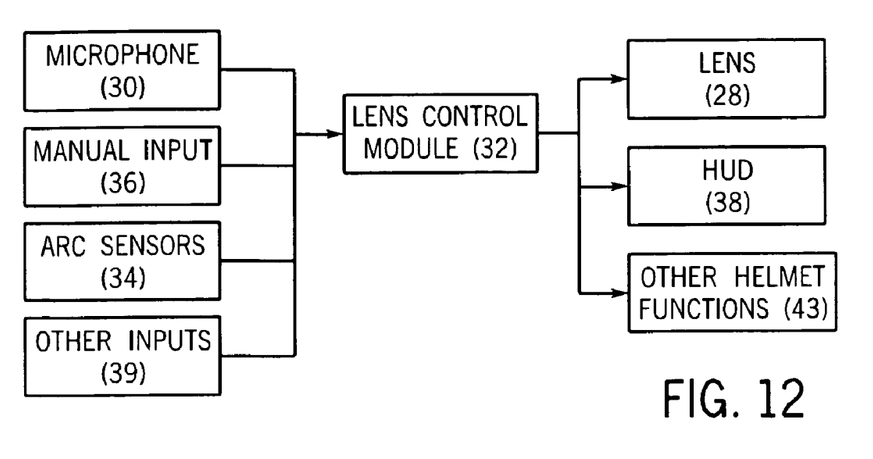
FIG. 12 is a diagrammatical illustration of the exemplary embodiment of the welding helmet of FIG. 11 in accordance with aspects of the present technique.

Similar to the limitations of adjusting the lens assembly 24, adjustment of additional helmet assembly functions may require removal of the helmet assembly 20, which may decrease the efficiency of the operator 18. Accordingly it may be desirable for the microphone 30 and lens control module 32 to control other functions of the welding helmet assembly 20. In one embodiment, the helmet assembly 20 may include an additional helmet function that may be controlled by the lens control module 32. For example, as depicted in FIG. 11, the welding helmet assembly 20 may include a fan 42 that may run at a variety of speeds. In one embodiment, the fan 42 may be controlled by an output of the lens control module 32 as depicted by the diagram of FIG. 12. The lens control module 32 may monitor inputs from the microphone 30, manual input 36, arc sensors 34, or other inputs 39, and send an appropriate control signal to the cooling fan 42 represented by the "other helmet functions" block 43 in the diagram of FIG. 12. For example, the operator 18 may speak the command "fan" and "up" into the microphone 30, wherein the lens control module 32 responds by transmitting a signal to increase the speed of the fan 42. As will be appreciated by a person of ordinary skill in the art, the control of other helmet functions 43 may include integration of all of the variations discussed previously, including the manipulation of the HUD 38 and the integration of the manual input 36. For example, the manual input may be coordinated with audible inputs to control the fan 42, all while the settings are updated on the HUD 38. As will also be appreciated by those skilled in the art, the other helmet functions 43 may include any functions desirable to implement into that helmet assembly. For example, the lens control module may control radio communication, an audio system, a helmet security system, or a respirator connection.

Figure 13:
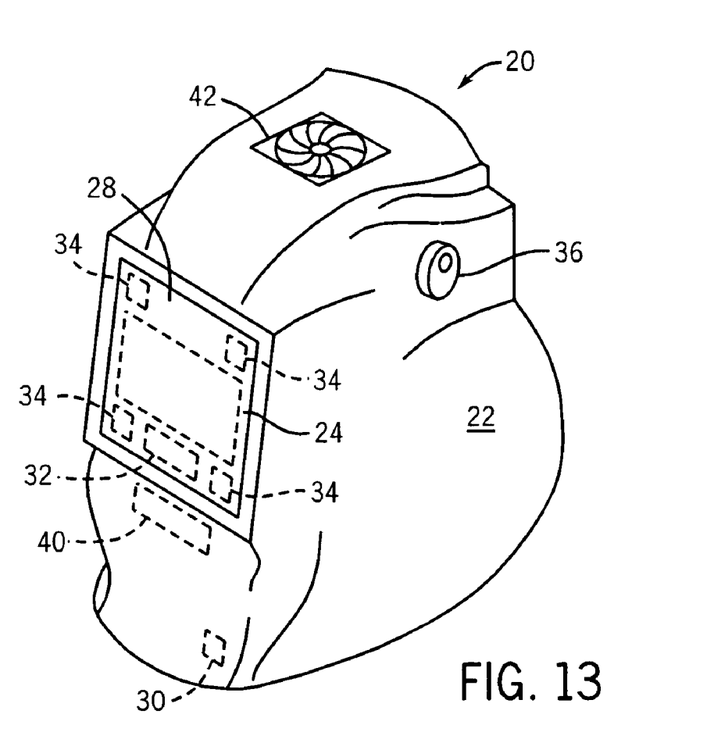
FIG. 13 is an illustration of yet another alternate exemplary embodiment of the welding helmet of FIG. 1 including a secondary control module accordance with aspects of the present technique.
Figure 14:
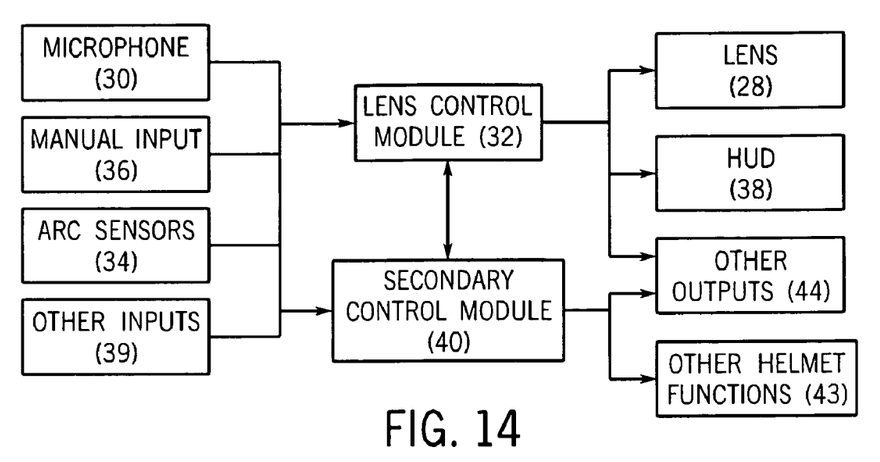
FIG. 14 is a diagrammatical illustration of the exemplary embodiment of the welding helmet of FIG. 13 in accordance with aspects of the present technique.

Previously, the discussion has focused on control of the welding helmet assembly 20 by a single lens control module 32. Although this configuration may prove beneficial, in some cases it may be desirable for additional control circuitry to be integrated into the helmet assembly 20. In one embodiment, the helmet assembly 20 may include the lens control module 32 as well as a secondary control module 40, as depicted in FIG. 13. For example, as depicted in the diagram of FIG. 14, the lens control module 32 and the secondary control module 40 may each receive inputs (e.g., microphone 30, manual input 36, arc sensors 34, or other inputs 39), wherein the lens control module 32 outputs control signals to the lens 28, the HUD 38, and other outputs 44 (e.g., power supply 12), while the secondary control module 40 controls other helmet functions 43 (e.g., fan speed). For example, in an embodiment, a control signal may be output to the power supply 12 to control functions of the power supply 12, including initiating welding in coordination with darkening the shade of the lens 28.

Figure 15:
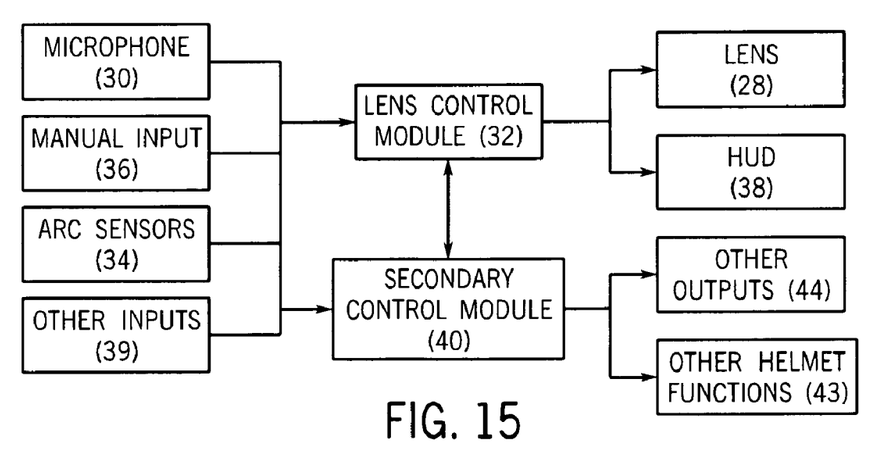
FIG. 15 is another diagrammatical illustration of the exemplary embodiment of the welding helmet of FIG. 13 configured to provide a modular lens assembly in accordance with aspects of the present technique.

A secondary control module may also provide for a modular helmet assembly wherein components such as the lens assembly 24 may be implemented as add-on features. In one embodiment, in contrast to the control system of FIG. 14, the lens control module 32 of FIG. 15 may be limited to controlling the lens 28 and the HUD 38, while the secondary control module is configured to control the other outputs 44 and the other helmet functions 43. For example, as depicted in the diagram of FIG. 15, the lens control module 32 may be provided as part of the lens assembly 24, and be configured to control functions of the lens 28 and arc sensors 34, while a secondary control module 40 transmits and receives signals related to functions of the helmet not directly connected to the lens assembly 24. In another embodiment, the lens control module 42 and the secondary control module 40 may share a signal to coordinate their responses. For example, the lens control module 42 may only receive inputs from the microphone 30 and arc sensors 34, while the secondary control module 40 receives and processes signals from the additional inputs (microphone 30, manual input 36, and other inputs 39). The lens control module 32 and the secondary control module 40 may then be configured to coordinate the signals output to the lens 28, HUD 38, other helmet functions 43 and other outputs (e.g., power supply 12). For example, the operator 18 may command into the microphone 30 a particular shade for the lens which is interpreted by voice recognition processing in the secondary control module 40. The secondary module may output the setting to an "other output" (e.g., remote control) and the lens control module 32. In response the lens control module 32 may send a signal to the HUD 38 to display the current shade setting, and signal the lens to change to the darkened shade only when the arc sensor 34 detects light in excess of a threshold value. As will be appreciated by those skilled in the art, such a configuration may allow for a helmet design to modularize the lens assembly 24. For example, an operator 18 may purchase a helmet assembly 20 with voice control of functions, and later add a lens assembly 24 that incorporates arc sensors 34 and a lens control module 32 to coordinate the HUD 38 and the lens 28 with the voice control processing. As will also be appreciated by those skilled in the art, the configuration of the helmet assembly 20 (inputs and outputs) may be modified and combined to provide the desired functionality and modularity within the welding system 10.

Due to the demand for welding helmets, and the increased cost of helmets that include a range of features described above, it may also be desirable for the welding helmet assembly 20 to incorporate a security system into the control circuitry. In one embodiment, the helmet assembly 20 may include security via the voice recognition. For example, upon powering on of the helmet assembly 20, the operator 18 may be required to speak a password to "unlock" the functionality of the helmet. The voice command sensed may then be compared to a previously recorded password, or stored audio data, to determine if the operator 18 is in fact an authorized operator 18 of the helmet assembly 20. In another embodiment, the voice recognition software may also compare the vocal patterns to ensure that the password was spoken by the correct operator 18.

To increase the level of flexibility for the helmet assembly 20, it my also be desirable that the operator 18 be capable of customizing the interface. In one embodiment, an interface may be provided between the helmet assembly 20 and a processing computer (PC). For example, the helmet assembly 20 may include a standard connection (e.g., a USB cable connection) to a processing computer that allows the operator 18 to modify the commands available, the helmet assembly response to commands, and/or the menu structure. In another embodiment, this functionality may be contained within the helmet. For example, the HUD 38 in coordination with other inputs (e.g., microphone 30, manual input 36) may be configured to provide for the operator 18 to modify the commands and menu structures. As would be appreciated by those skilled in the art, customizing the interface may take a multitude of forms, and include various implementations of functionality.

While only certain features of the invention have been illustrated and described herein, many modifications and changes will occur to those skilled in the art. It is, therefore, to be understood that the appended claims are intended to cover all such modifications and changes as fall within the true spirit of the invention.

| ELEMENT LIST | |
|---|---|
| 10 | Welding System |
| 12 | Power Supply |
| 14 | Conduit |
| 16 | Electrode |
| 18 | Operator |
| 20 | Helmet Assembly |
| 22 | Helmet Shell |
| 24 | Lens Assembly |
| 26 | Arc |
| 28 | Lens |
| 30 | Microphone |
| 32 | Lens Control Module |
| 34 | Arc Sensor |
| 36 | Manual Input |
| 37 | Remote Control |
| 38 | Heads Up Display |
| 39 | Other Inputs |
| 40 | Secondary Control Module |
| 42 | Fan |
| 43 | Other Helmet Functions |
| 44 | Other Outputs |

The invention claimed is:

1. A welding helmet comprising:
a helmet shell;
an electronically controllable lens supported by the shell;
a microphone supported by the helmet shell and configured to receive an audible input and to generate a signal in response to the audible input received;
a non-audible manual input device configured to receive a manual input and to generate a second signal in response to the manual input received, wherein the manual input and the audible input are configured to cooperatively define a function of the manual input; and
an electronic control module coupled to the lens, to the microphone, and to the non-audible manual input device and configured to control the electronically controllable lens based upon the signal and the second signal.

2. The welding helmet of claim 1, wherein the electronically controllable lens is configured to transition the lens between light and dark state based upon an audible command sensed by the microphone.

3. The welding helmet of claim 1, wherein the electronic control module includes a memory circuit for storing at least one parameter setting based upon the signal from the microphone.

4. The welding helmet of claim 3, wherein the at least one parameter comprises the shade level of the darkened state of the electronically controllable lens.

5. The welding helmet of claim 3, wherein the at least one parameter comprises the sensitivity to light produced during welding.

6. The welding helmet of claim 3, wherein the at least one parameter comprises the delay in transition from a dark state to a light state after the electronic control module determines that a welding arc has been extinguished.

7. The welding helmet of claim 1, wherein the audible input and the manual input are utilized by the electronic control module to simultaneously adjust a function and a setting of the electronically controllable lens.

8. The welding helmet of claim 1, wherein the manual input device comprises at least one of a knob, a dial, a button, a touch-sensitive sensor, or a remote control.

9. The welding helmet of claim 7, wherein the function is a shade of the electronically controllable lens and the setting is a degree of shade of the electronically controllable lens.

10. The welding helmet of claim 1, wherein the electronically controllable lens and the electronic control module are integral to a lens subassembly.

11. The welding helmet of claim 1, wherein the electronically controllable lens, the electronic control module and the microphone are integral to a lens subassembly.

12. The welding helmet of claim 1, wherein the lens comprises at least one photodetector for detecting light from a welding arc, the photodetector being coupled to the electronic control module to cause transition of the lens between light and dark states based upon light detected by the photodetector and at least one parameter based upon the signal from the microphone.

13. The welding helmet of claim 1, wherein the lens comprises at least one electromagnetic sensor for detecting electromagnetic emissions from a welding arc, the electromagnetic sensor being coupled to the electronic control module to cause transition of the lens between light and dark states based upon emissions detected by the electromagnetic sensor and at least one parameter based upon the signal from the microphone.

14. The welding helmet of claim 1, wherein the electronic control module comprises a processor configured to perform voice recognition processing on the signal.

15. The welding helmet of claim 14, wherein voice recognition processing comprises comparing the audible input signal to previously stored audio data.

16. The welding helmet of claim 1, wherein the microphone comprises a processor configured to perform voice recognition processing on the audible input received.

17. The welding helmet of claim 1, wherein the electronic control module is configured to control at least one function of the welding helmet in addition to controlling the electronically controllable lens.

18. The welding helmet of claim 1, comprising a secondary control module configured to control functions of the helmet other than the electronically controllable lens.

19. The welding helmet of claim 1, wherein the electronic control module is configured to issue an operational parameter to a welding system.

20. The welding helmet of claim 19, wherein the operational parameter comprises a command to a power supply to initiate a weld.

21. The welding helmet of claim 1, wherein the welding helmet is configured to remain inoperative to a user until a voice recognition processor confirms the voice pattern or password of an authorized operator.

22. The welding helmet of claim 1, wherein the welding helmet is configured to allow a user to manipulate a relationship between the audible input and an output by the electronic control module control.

23. The welding helmet of claim 22, wherein manipulating the relationship is configured to be performed through an external interface to a processing computer.

24. The welding helmet of claim 1, wherein the electronic control module is configured to set a value for at least one parameter of the welding helmet based at least partially upon the signal.

* * * * *